(12) United States Patent
Yamane (10) Patent No.: US 8,382,661 B2
(45) Date of Patent: Feb. 26, 2013

(54) ENDOSCOPE SUCKING OPERATION APPARATUS

(75) Inventor: Kenji Yamane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 759 days.

(21) Appl. No.: 12/542,832

(22) Filed: Aug. 18, 2009

(65) Prior Publication Data

US 2010/0049001 A1    Feb. 25, 2010

(30) Foreign Application Priority Data

Aug. 22, 2008 (JP) ................. 2008-213918

(51) Int. Cl.
*A61B 1/12* (2006.01)
(52) U.S. Cl. .................. 600/159; 600/156; 600/158
(58) Field of Classification Search .............. 600/159
See application file for complete search history.

(56) References Cited

U.S. PATENT DOCUMENTS

| | | | | |
|---|---|---|---|---|
| 691,569 A | * | 1/1902 | Pohlman | 251/246 |
| 4,061,250 A | * | 12/1977 | Tada | 222/321.8 |
| 5,857,596 A | * | 1/1999 | Lee | 222/509 |
| 6,425,498 B1 | * | 7/2002 | Gheorgheos | 222/78 |
| 2008/0027283 A1 | * | 1/2008 | Matsui et al. | 600/127 |

FOREIGN PATENT DOCUMENTS

| | | |
|---|---|---|
| JP | 2-88602 | 7/1990 |
| JP | 2001-157663 A | 6/2001 |
| JP | 2003-325442 A | 11/2003 |
| JP | 2008-29527 | 2/2008 |

* cited by examiner

*Primary Examiner* — Matthew J Kasztejna
*Assistant Examiner* — Alexandra Newton
(74) *Attorney, Agent, or Firm* — Birch, Stewart, Kolasch & Birch, LLP (57) ABSTRACT

When a suction button is pushed in a pushing operation direction, the suction button pushes down longer lever ends of inversion levers, shorter lever ends of the inversion levers are pushed up based on a seesaw operation and the principle of leverage, and a piston body coupled through a coupling body moves in a direction opposed to a pushing operation direction against an urging force of a spring in cooperation with this upward movement. As a result, a valve moving portion moves away from a valve receiving portion to open a suction duct valve portion and suction is carried out, but the piston body retires to an outer periphery side of a bent duct when the valve portion is opened, and hence a suction duct is widened, thereby facilitating suction of even, e.g., a fluid having high viscosity.

5 Claims, 6 Drawing Sheets

ENDOSCOPE SUCKING OPERATION APPARATUS

The disclosure of Japanese Patent Applications No. 2008-213918, filed on Aug. 22, 2008, including its specification, claims and drawings, is incorporated herein by reference in its entirety.

BACKGROUND OF THE INVENTION

1. Field of the Invention

The present invention relates to an endoscope sucking operation apparatus, and more particularly to a configuration of a sucking operation apparatus that moves a piston body from a valve portion to open a suction duct (conduit) by performing a pushing operation with respect to a suction button provided to an operating portion.

2. Description of the Related Art

Figure 5:
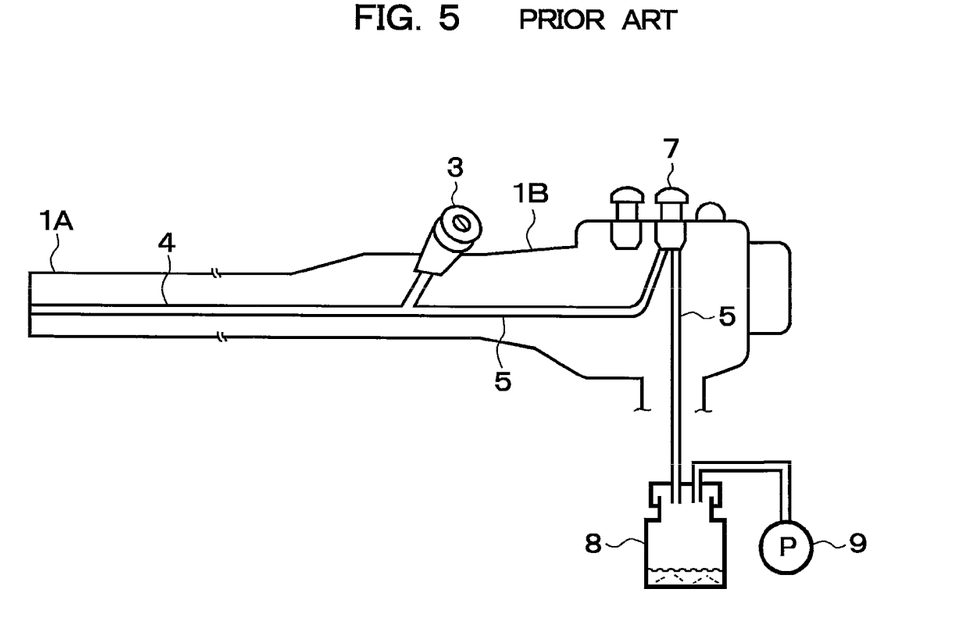
FIG. 5 is a view showing a configuration concerning suction of a conventional endoscope.

FIG. 5 shows a configuration of a conventional endoscope apparatus, an endoscope has, e.g., a distal end portion 1A including an objective optical system, a solid-state image sensing device, and others, an operating portion 1B provided through a bending portion, and others, a forceps opening (a treatment instrument insertion channel introduction opening) 3 is provided in this operating portion 1B, and a treatment instrument insertion channel 4 is arranged to extend from this forceps opening 3 to a distal end surface of the distal end portion 1A. A suction tube (a duct) 5 through which a fluid (contents) or the like in an observation target is sucked is connected with this treatment instruction insertion channel 4 so that the treatment instrument insertion channel 4 can also function as a suction duct. Further, a suction button 7 is arranged on the operating portion 1B, and a suction pump 9 is connected to the suction tube 5 through a liquid storage tank 8.

Figure 6A:
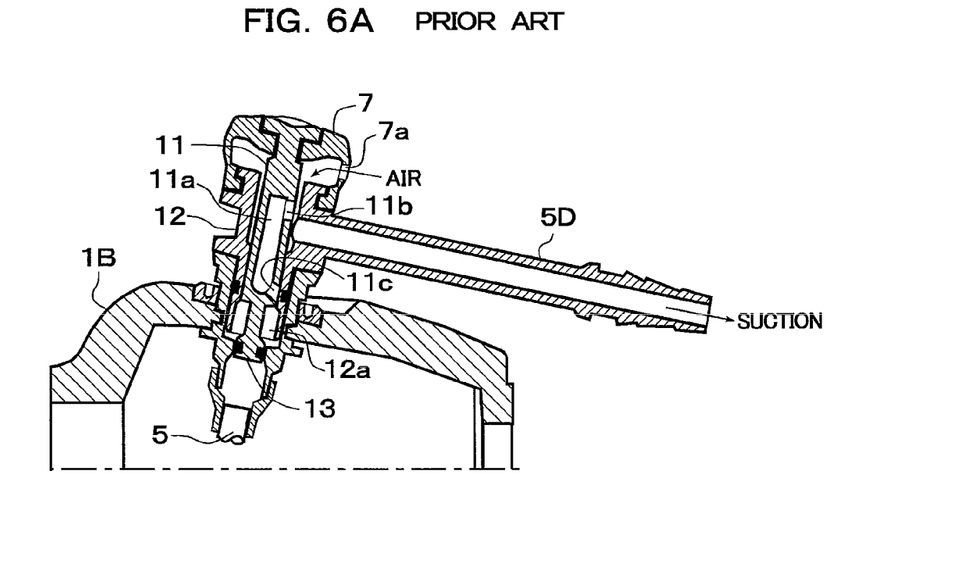
FIG. 6A is a cross-sectional view showing a configuration of a convention endoscope sucking operation apparatus in a non-operated state.
Figure 6B:
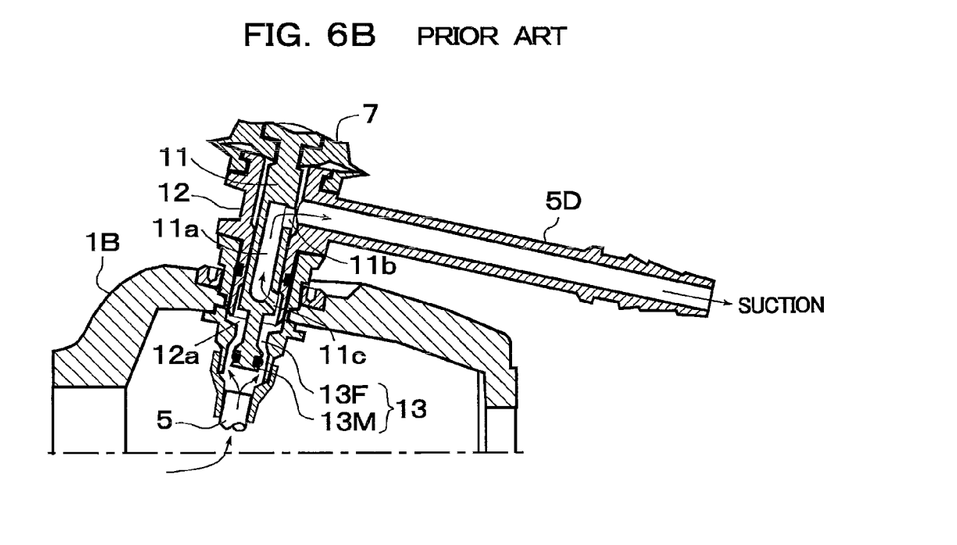
FIG. 6B is a cross-sectional view showing an operated state of the conventional apparatus.

FIGS. 6A and B show a configuration of a sucking operation apparatus including the suction button 7, and this example is suggested for a portable endoscope. As shown in the drawings, in this sucking operation apparatus, a piston body 11 is integrally disposed at the center of the suction button 7 formed of an elastic body, and this piston body 11 is arranged to move up and down through a circular inner path 12a of a support main body 12. The suction button 7 can upwardly urge the piston body 11 by using its elastic force, and an opening portion 7a is provided in its side surface. The piston body 11 has an inner path 11a and openings 11b and 11c, and a valve portion 13 that closes the suction duct when the piston body 11 is appressed against a path inner wall of the support main body 12 is provided to the piston body 11 and the support main body 12. It is to be noted that the suction tube 5 on the endoscope distal end side is connected to the lower side of the inner path 12a of the support main body 12 and a suction connecting tube 5D that is used to connect the tank-side suction tube 5 is formed on a side surface of the support main body 12.

According to such a sucking operation apparatus for an endoscope, when a sucking operation is not performed as shown in FIG. 6A, air is sucked from the opening 7a of the suction button 7 based on the suction of the suction pump 9, and the valve portion 13 is closed, and hence suction is not performed from the distal-end-side suction tube 5. On the other hand, when the suction button 7 is pressed, since the piston body 11 moves down and the valve portion 13 and the opening 11c are opened, a liquid (contents) or the like of an observation target is sucked through the treatment instruction insertion channel 4 and the suction tube 5 by a sucking operation of the suction pump 9, and this liquid or the like is discharged to the storage tank 8.

However, in the conventional endoscope sucking operation apparatus, as shown in FIG. 6B, a path between the piston body 11 and the support main body 12 in the valve portion 13 is narrow, and a fluid or the like having less viscosity can be sufficiently sucked, but there occurs a problem that the narrow path in this valve portion 13 may be clogged when sucking a material having high viscosity such as phlegm. That is, in the valve portion 13, the piston body 11 itself (a shaft) remains in a path of a valve receiving portion 13F (a receiving portion of a valve moving portion 13M of the piston body 11) of the support main body 12 even when the valve portion 13 is opened, and the suction duct through which the fluid passes is narrowed due to presence of this piston body 11.

In view of the above-described problem, it is an object of the present invention to provide the endoscope sucking operation apparatus that can readily suck, e.g., a fluid having high viscosity without narrowing the path between the piston body and the support main body in the valve portion of the suction duct.

SUMMARY OF THE INVENTION

To achieve this object, according to an aspect of the present invention, there is provided an endoscope sucking operation apparatus that opens a valve portion provided in a suction duct by performing a pushing operation with respect to a suction button of an endoscope operating portion, comprising: a piston body that closes the suction duct valve portion when urged in a direction of the pushing operation of the suction button and opens the suction duct valve portion when moved from the closing position toward the suction button side; and an inversion movement mechanism that cooperates with the pushing operation of the suction button to move the piston body in a direction opposed to the direction of the pushing operation, wherein the suction duct valve portion is closed when the suction button is not operated, and the suction duct valve portion is moved in the direction opposed to the direction of the pushing operation against an urging force of the piston body to be opened when the suction button is pushed. That is, it is configured to close the suction duct valve portion by urging the piston body in a direction of the pushing operation and to open it by moving the piston body in the direction opposed to the direction of the pushing operation.

Here, as the inversion movement mechanism, an inversion lever that performs a seesaw operation is arranged on substantially the same axis as an axis of the operating direction of the suction button, and an operation end of the suction button can be coupled with one end of this inversion lever whilst an operation end of the piston body can be coupled with the other end of the same.

According to such a configuration, when the suction button is pushed, for example, the inversion level coupled with this suction button performs the seesaw operation, and the piston body coupled with the other end of this inversion level moves in the direction opposed to the direction of the pushing operation, thereby opening the suction duct valve portion. When this valve portion is opened, the piston body itself including the valve moving portion moves away from the valve receiving portion of the suction duct valve portion, the piston body does not partially remains in the valve receiving portion as different from the conventional example, and the opening of the valve receiving portion for the suction duct is widened, thus easily sucking, e.g., a fluid having high viscosity.

The endoscope sucking operation apparatus according to the present invention has an effect that even a fluid having high viscosity such as phlegm can be easily sucked without narrowing the path between the piston body and the support main body in the valve portion of the suction duct. Furthermore, in the sucking operation, the pushing operation performed by using one hand can be maintained like the conventional example. That is, the valve portion can be likewise opened by pulling the piston body in a pulling operation as an operation in a direction opposite to that of the pushing operation irrespective of the inversion movement mechanism, but effecting this pulling operation by one hand is substantially difficult, and the pushing operation that can be easily executed by one hand is maintained in the present invention.

Moreover, there can be also obtained an advantage that the coaxial arrangement of the inversion lever enables excellently maintaining the suction operability when carrying out the pushing operation. That is, an operation level having an inverted V shape may be provided and the piston body may be coupled with one end of the operation level while arranging a swiveling axis at a bent portion of this operation level to push the other end of the operation lever, but the other end of the operation level is arranged to protrude in a predetermined direction from a predetermined position of the endoscope operating portion (a position of the piston body), thus degrading the operability. According to the present invention having the above-described configuration, the sucking operation can be performed by the conventional pushing operation using the push button without adopting such an operation lever.

Additionally, according to another aspect of the present invention, the piston body is arranged so as to reciprocate in an operating direction path (or a longitudinal path) formed in the support main body, a bent duct formed to be bent from the operating direction path toward a support main body side surface is provided to this support main body as the suction duct, a valve receiving portion is arranged at a proximal end of this bent duct on the operating direction path side, and the valve receiving portion and a valve moving portion provided below the piston body constitute a suction duct valve portion.

According to the configuration of another aspect of the present invention, when the suction duct valve portion is opened, since the valve moving portion of the piston body moves to an outer periphery side of the bent duct from the valve receiving portion provided at the proximal end of the bent duct on the operating direction path side, the bent duct is wide opened to facilitate passage of, e.g., a fluid.

Further, since the suction duct valve portion is arranged in the bent duct, the simple configuration can obtain an effect that the path can be assuredly widened when the suction duct valve portion is opened.

DETAILED DESCRIPTION OF THE PREFERRED EMBODIMENTS

Figure 1:
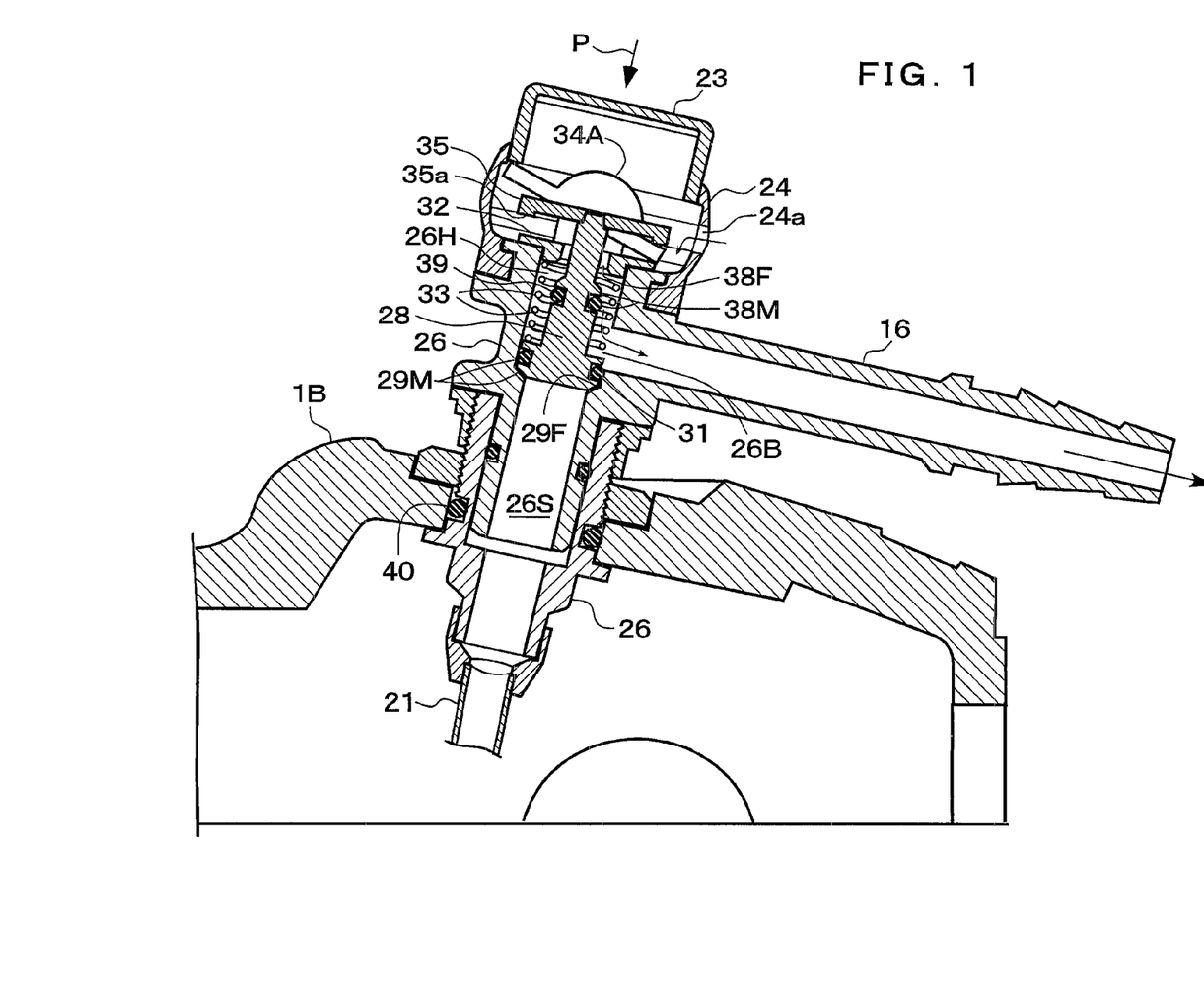
FIG. 1 is a cross-sectional view showing a configuration of an endoscope sucking operation apparatus according to an embodiment of the present invention in a non-operated state.
Figure 2:
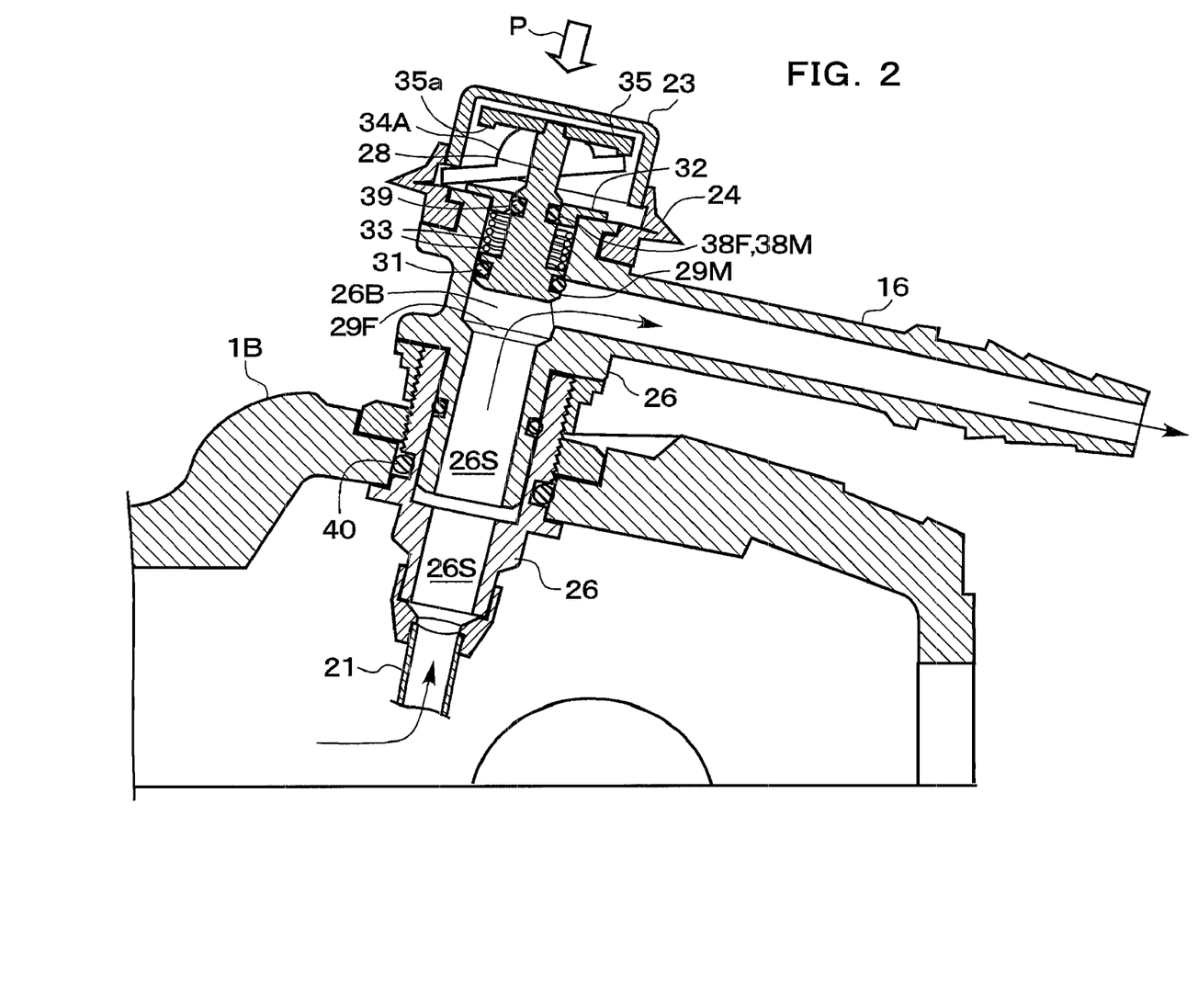
FIG. 2 is a cross-sectional view showing a configuration of the sucking operation apparatus according to the embodiment in an operated state.
Figure 3:
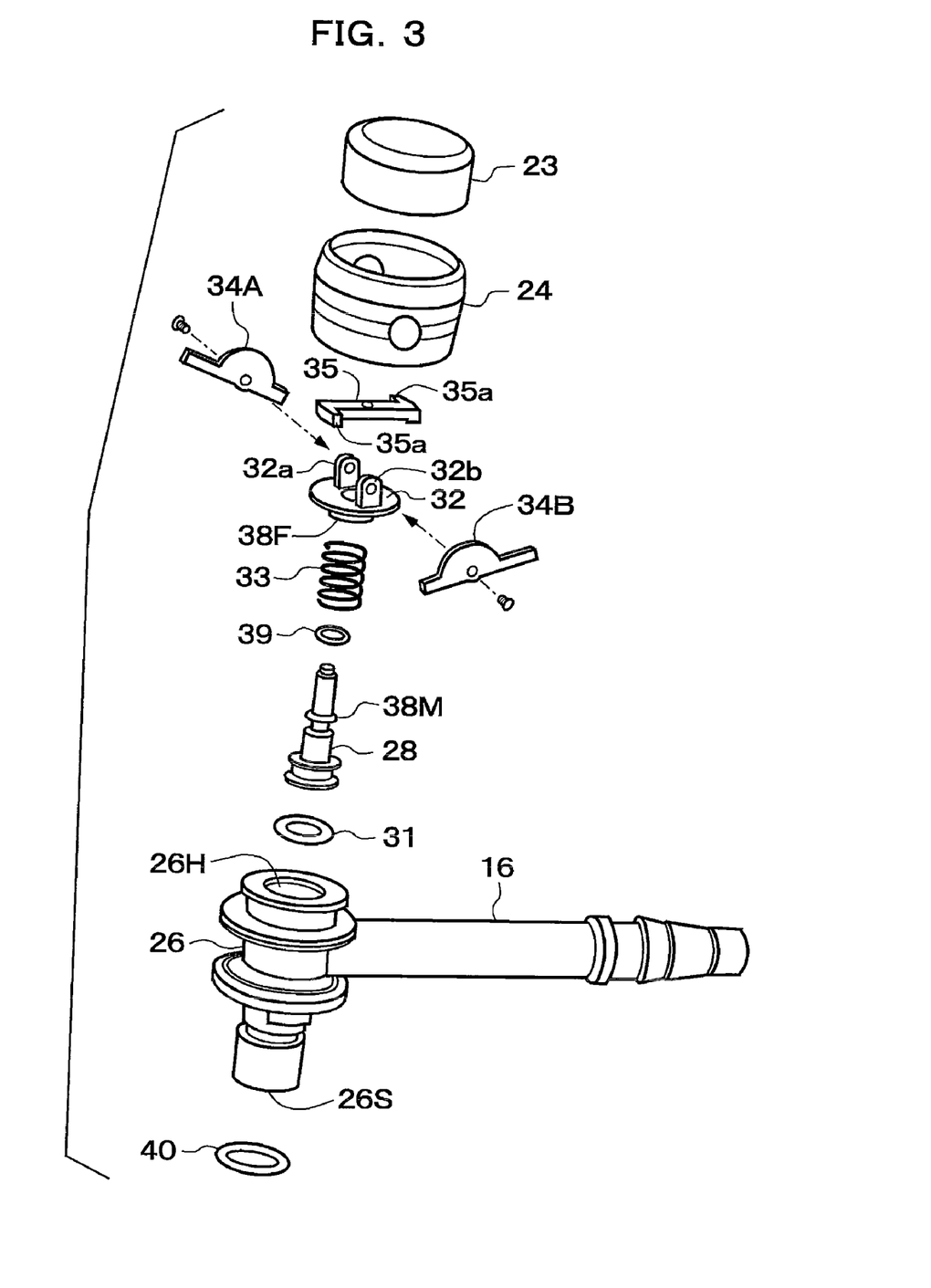
FIG. 3 is an exploded perspective view showing each structure in the sucking operation apparatus according to the embodiment.
Figure 4:
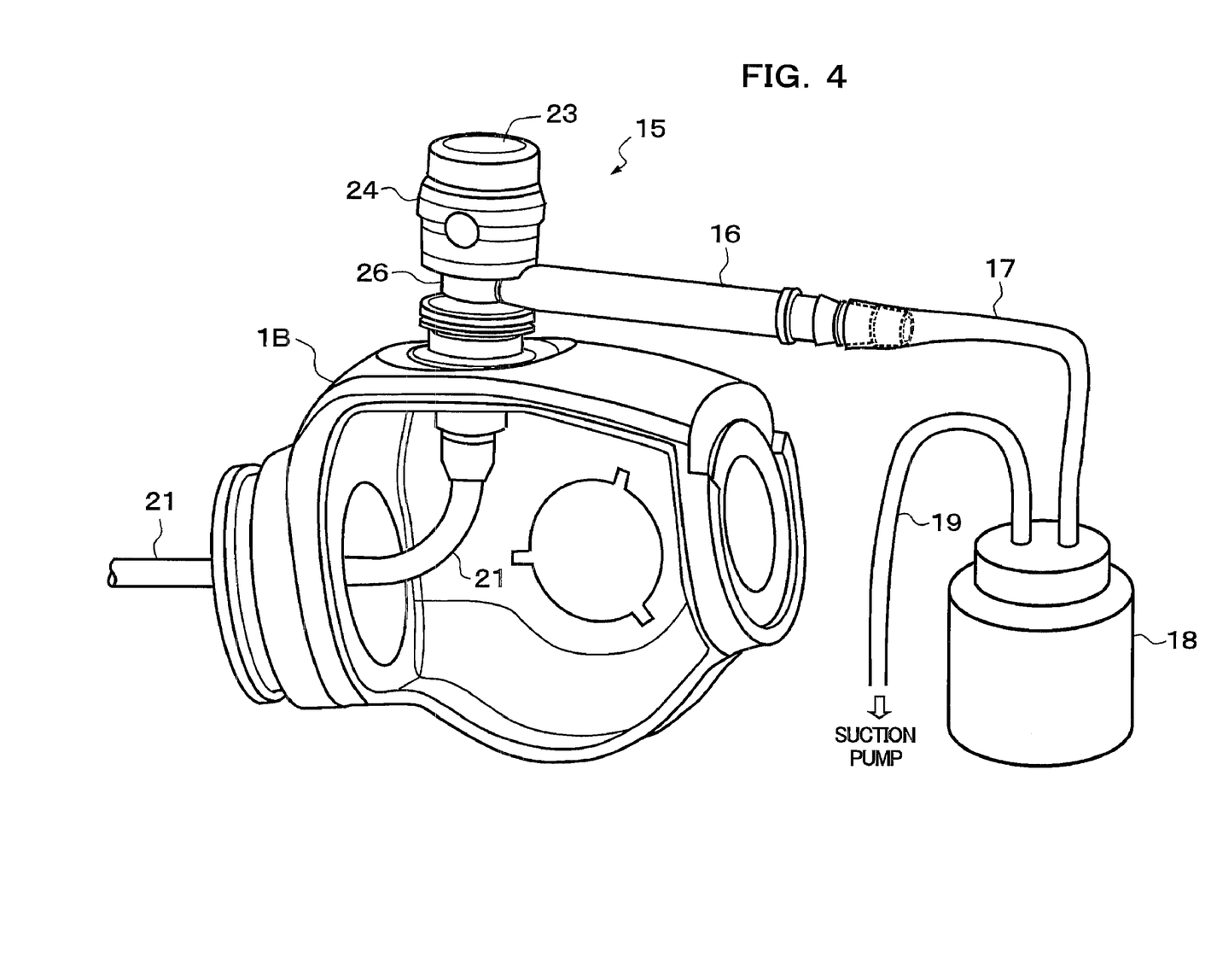
FIG. 4 is a perspective view showing configurations of the sucking operation apparatus and a storage tank according to the embodiment.

FIGS. 1 to 4 show a configuration of an endoscope sucking operation apparatus according to an embodiment, wherein FIGS. 1 and 2 are cross-sectional views of the sucking operation apparatus, FIG. 3 is an exploded view of the sucking operation apparatus, and FIG. 4 shows an entire configuration including a suction tank. As shown in FIG. 4, the sucking operation apparatus 15 according to the embodiment is applied to, e.g., a portable endoscope, the sucking operation apparatus 15 is arranged in an endoscope operating portion 1C, a suction connecting pipe 16 of this suction operating apparatus 15 is connected with a liquid storage tank 18 through a suction tube 17, and a suction pump is connected with this storage tank 18 via a suction tube 19. On the other hand, a suction tube 21 on an endoscope distal end side arranged in an endoscope operating portion 1B is connected with this suction operating apparatus 15.

As shown in FIGS. 1 to 3, in the sucking operation apparatus 15, a suction button 23 that performs a pushing operation, a holding portion 24 that holds this suction button 23 and is formed of a cylindrical elastic member that expands and contracts in an operating direction (a pushing operation direction P and an opposite direction thereof) of this suction button 23, and a support main body 26 that holds this holding portion 24 are provided, and an opening 24a through which air is flowed in is formed in the holding portion 24. A piston body 28 is arranged in the support main body 26 so as to reciprocate in the operating direction (a longitudinal direction) of the suction button 23, an air path 26H is formed on an outer periphery side of this piston body 28, and an inner path 26S that communicates with this air path 26H to function as a suction duct is formed.

Further, a bent duct 26B that is bent from this inner path 26S to a side surface of the support main body 26 is formed, and the suction connecting pipe 16 is arranged to communicate with this bent duct 26B. Furthermore, a valve receiving portion 29F is provided at a proximal end of the bent duct 26B on the inner path 26S side, and a valve moving portion 29M having an O-ring 31 is provided at a lower end of the piston body 28 so as to be appressed against this valve receiving portion 29F and close the inner path (the suction duct) 26S.

A support fixing plate 32 having a discoid shape and a central through hole is fixed/arranged on an upper surface portion of the support main body 26, and a coil spring 33 that urges this piston body 28 in the pushing operation direction P with respect to the support fixing plate 32 is provided between this support fixing plate 32 and the lower end portion of the piston body 28. This support fixing plate 32 also functions as a support portion for inversion levers 34A and 34B, and swiveling axes of the inversion levers 34A and 34B are pivotally supported by axis support portions 32a and 32b. That is, the swiveling axis of each of the inversion levers 34A and 34B is arranged to be substantially coaxial with an axis of the suction button 23 in the operating direction or an axis of the piston body 28, and a lever length from the swivel axis to one end is short whilst a lever length to the other end is long in order to perform an inverting operation based on the principle of leverage.

On the other hand, a coupling body 35 is disposed and fixed to an upper portion of the piston body 28 so as to be placed on the upper side of this support fixing plate 32, and this coupling body 35 is arranged in such a manner that short lever ends of the corresponding inversion levers 34A and 34B are engaged/coupled with two engagement claws 35a protruding in the horizontal direction at both ends of the coupling body 35. A lower end portion of the suction button 23 is engaged/coupled with the longer lever ends of the inversion levers 34A and 35B, and the inversion levers 34A and 34B move the piston body 28 to the opposite side of the pushing operation direction P through the coupling body 35 based on the pushing operation of the suction button 23.

Furthermore, a valve receiving portion 38F of an air path valve portion is provided on the lower side of the central opening of the support fixing plate 32, and a valve moving portion 38M having an O-ring 39 is provided in an intermediate portion of the piston body 28 so as to be appressed against this valve receiving portion 38F and close the air path 26H. It is to be noted that an O-ring 40 that maintains water tightness between an outer periphery of the support main body 26 on the lower side and a case body of the endoscope operating portion 1B is provided on this outer periphery.

The embodiment has the above-explained configuration, and suction is performed from the suction pump through the storage tank 18, the suction tube 17, and the suction connecting pipe 16 depicted in FIG. 4 when an endoscope is used, but the valve moving portion 29M and the valve receiving portion 29F of the suction duct valve portion are closed and the valve moving portion 38M is away from the valve receiving portion 38F to be opened in the air path valve portion when the suction operation is not performed as shown in FIG. 1, and hence air that has flowed in from the opening 24a of the holding portion 24 passes through the air path 26H in the support main body 26 to be led to the suction connecting pipe 16.

On the other hand, as shown in FIG. 2, when the suction button 23 is pushed in the pushing operation direction P, this suction button 23 pushes down the long lever ends of the inversion levers 34A and 34B, and the short lever ends of the inversion levers 34A and 34B move up based on the seesaw operation and the principle of leverage, whereby the piston body 28 coupled through the coupling body 35 moves (reciprocates) in the direction opposite to the pushing operation direction P against a urging force of the spring 33. At this time, the valve moving portion 29M for the suction duct moves away from the valve receiving portion 29F to open the suction duct valve portion, a fluid or the like in an observation target is sucked from the treatment instrument channel at the endoscope distal end portion, and this fluid or the like is discharged into the storage tank 18 via the distal end-side suction duct 21, the inner path 26S, the bent duct 26B, the suction connecting pipe 16, and the suction tube 17. Thereafter, when the suction button 23 is released, the spring 33 pushes down the piston body 28, and the suction button 23 automatically returns to its original position.

As explained above, at the time of the sucking operation, as can be understood from FIG. 2, since the piston body 28 (the valve moving portion 29M) retires to the outer periphery side (the duct lateral surface side on the upper side in the drawing) of the bent duct 26B from the valve receiving portion 29F, a shaft or the like of the piston body 28 does not remain in the duct as different fro the conventional example, and the suction duct can be widened to excellently suck a fluid or the like having high viscosity such as phlegm. Moreover, in the embodiment, when the valve portion is opened, the O-ring 31 of the valve moving portion 29M is pressed against the inner wall of the air path 26H to maintain a watertight state in such a manner that the fluid or the like flowing through the bent duct 26B can be prevented from leaking toward the air path 26H side. It is to be noted that this configuration that the valve moving portion 29M is pressed against the inner wall of the air path 26H also functions as a valve portion of the air path 26H.

In the foregoing embodiment, to move the piston body 28 in the direction opposite to the pushing operation direction P, a swiveling axis of a bent portion of each operation lever (a driving lever) having an inverted V shape may be disposed to a position apart from the axis of the suction button 23 in the operating direction, and a shorter end (a driving end) of this operation lever may be coupled with the piston body so that the other end of the same can perform the pushing operation as a suction operating portion. However, in such a configuration, the suction operating portion as the other end of the operation lever is arranged to protrude in a predetermined direction from a current position of the suction button 23, which degrades the operability. In the embodiment, the swiveling axes of the inversion levers 34A and 34B are arranged substantially coaxially with the axis of the suction button 23 in the operating direction, thereby excellently maintaining the operability of the suction button 23.

DESCRIPTION OF SYMBOLS 7, 23 SUCTION BUTTON 11, 28 PISTON BODY
12, 26 SUPPORT MAIN BODY
5, 21 SUCTION TUBE 26B BENT DUCT
29F, 38F VALVE RECEIVING PORTION
29M, 38M VALVE MOVING PORTION
33 SPRING 34A, 34B INVERSION LEVER

CITATION LIST

Patent Document 1: JP-A-2001-157663
Patent Document 2: JP-A-2003-325442

What is claimed is:
1. An endoscope sucking operation apparatus comprising:
a suction duct valve portion that opens a suction duct when a pushing operation is performed with respect to a suction button of an endoscope operating portion;
a piston body which closes the suction duct valve portion when urged in a pushing operation direction of the suction button and opens the suction duct valve portion when moved toward the suction button side from a closing position; and
an inversion movement mechanism that cooperates with the pushing operation of the suction button and moves the piston body in a direction opposite to the pushing operation direction,
wherein the inversion movement mechanism comprises an inversion lever that performs a seesaw operation arranged coaxially with an axis of the suction button in an operating direction, and an operation end of the suction button is coupled with one end of the inversion lever whilst an operation end of the piston body is coupled with the other end of the inversion lever,
wherein an axis of the suction button in the operating direction is arranged to be substantially coaxial with an axis of the piston body, and
wherein the suction duct valve portion is closed when the suction button is not operated, and the suction duct valve portion is moved in the direction opposite to the pushing operation direction against an urging force of the piston body to be opened when the pushing operation is performed with respect to the suction button.

2. The endoscope sucking operation apparatus according to claim 1, wherein the piston body is arranged so as to reciprocate with respect to an operating direction path formed in a support main body, a bent duct formed to be bent toward a support main body side surface from the operating direction path is provided as the suction duct, a valve receiving portion is arranged at a proximal end of the bent duct on the operating direction path side, and the valve receiving portion and a valve moving portion provided below the piston body constitute the suction duct valve portion.

3. The endoscope sucking operation apparatus according to claim 1, wherein the piston body is arranged so as to reciprocate with respect to a longitudinal path formed in a support main body;
wherein the apparatus further comprises a bent duct provided as the suction duct, the bent duct formed to be bent from the longitudinal path toward a side surface of the support main body at a substantially right angle; and
wherein the suction duct valve portion opens/closes a valve through the bent duct when a valve moving portion performs an opening/closing operation, a valve receiving portion being arranged at a proximal end of the bent duct on the longitudinal path side, the valve moving portion being provided at a lower portion of the piston body so as to be pressed to the valve receiving portion when the suction duct valve portion is closed.

4. The endoscope sucking operation apparatus according to claim 1,
wherein the inversion movement mechanism comprises a pair of inversion levers which are arranged on both sides of the axis of the piston body, which operate by the principle of leverage, each of the inversion levers having a short lever end and a long lever end,
wherein the endoscope sucking operation apparatus further comprises a coupling body that couples the short lever ends of the inversion levers and the axis of the piston body, and
wherein when the suction button pushes down the long lever ends of the inversion levers, the piston body moves in the direction opposite to the pushing operation direction through the coupling body.

5. The endoscope sucking operation apparatus according to claim 4,
wherein the coupling body has engagement claws protruding in the horizontal direction at its both ends, and the short lever ends of inversion levers are arranged with the engagement claws.

* * * * *